United States Patent [19]

McNeal

[11] Patent Number: 5,734,468
[45] Date of Patent: Mar. 31, 1998

[54] PROBE AND METHOD FOR DETERMINING SERUM INDICES OF A SERUM SAMPLE

[75] Inventor: Jack D. McNeal, Long Beach, Calif.

[73] Assignee: Beckman Instruments, Inc., Fullerton, Calif.

[21] Appl. No.: 748,232

[22] Filed: Nov. 12, 1996

Related U.S. Application Data

[63] Continuation-in-part of Ser. No. 516,566, Aug. 18, 1995, abandoned.

[51] Int. Cl.⁶ .............. G01J 3/42; G01N 21/01
[52] U.S. Cl. .......................... 356/319; 356/244
[58] Field of Search .................. 356/213, 246, 356/436, 440, 319, 445; 250/43 LR, 435, 576; 422/81, 82.05, 82.06, 82.09, 91, 64, 67, 63; 436/164, 52, 45, 48, 49, 43

[56] References Cited

U.S. PATENT DOCUMENTS

| | | | |
|---|---|---|---|
| 3,263,554 | 8/1966 | Pickels | 88/14 |
| 3,573,470 | 4/1971 | Haley | 250/218 |
| 3,781,116 | 12/1973 | Jones | 356/180 |
| 4,169,125 | 9/1979 | Rodriguez et al. | 422/65 |
| 4,440,497 | 4/1984 | Carey et al. | 356/246 |
| 4,456,581 | 6/1984 | Edelmann et al. | 422/72 |
| 4,588,893 | 5/1986 | Vidrine et al. | 250/428 |
| 4,728,190 | 3/1988 | Knollenberg | 356/336 |
| 5,181,082 | 1/1993 | Jeanotte et al. | 356/436 |
| 5,241,368 | 8/1993 | Ponstingl et al. | 356/436 |
| 5,314,825 | 5/1994 | Weyrauch et al. | 436/43 |
| 5,407,638 | 4/1995 | Wang | 422/82.09 |
| 5,561,069 | 10/1996 | Brigham-Burke et al. | 436/518 |

FOREIGN PATENT DOCUMENTS 0201824  11/1986  European Pat. Off. ....... G01N 21/05

*Primary Examiner*—Frank G. Font
*Assistant Examiner*—Michael P. Stafira
*Attorney, Agent, or Firm*—William H. May; P. R. Harder; Steven G. Roeder

[57] ABSTRACT

A method and device for detecting the presence of hemolysis, icteris and lipemia in a serum sample are provided herein. The method includes the steps of positioning a probe inlet of a probe in a sample container, aspirating at least a portion of the serum sample into a probe lumen of the probe from the sample container, and monitoring the serum sample in a probe lumen to determine whether hemolysis, icteris and lipemia are present in the serum sample. The serum sample is monitored with a detector which performs spectrophotometric analysis of the serum sample in the probe lumen through a substantially transparent section of the probe. From the spectrophotometric analysis, a hemolytic index, an icteric index and a lipemic index of the serum sample can be established. Based upon these serum indices, the serum sample can be transferred to a clinical analyzer for additional tests or can be disposed of because the sample is compromised.

28 Claims, 3 Drawing Sheets

PROBE AND METHOD FOR DETERMINING SERUM INDICES OF A SERUM SAMPLE

This application is a continuation-in-part of application Ser. No. 08/516,566, filed Aug. 18, 1995, (now abandoned) which is incorporated herein by reference.

BACKGROUND OF THE INVENTION

1. Field of the Invention

The present invention relates to a method and device for determining the presence of Hemolysis, Icteris and Lipemia in a serum sample. The present invention is particularly useful for establishing a hemolytic index, an icteric index and a lipemic index for a serum sample, prior to transferring the serum sample to a clinical analyzer.

2. Relevant Background Information

The accurate analysis of a serum sample is often instrumental in determining the health of a patient and what measures are necessary to restore the health of the patient. In an effort to reduce laboratory labor costs, many hospitals and laboratories utilize automated clinical analyzers to analyze patient serum samples.

These clinical analyzers commonly utilize a plurality of cuvettes which are sequentially subjected to a variety of tests during a machine cycle of the clinical analyzer. Typically, during a machine cycle, the testing begins at one location, samples are added at one location and multiple serum samples are sequentially tested.

Clinical analyzers are presently able to accurately and quickly perform such functions as drug analysis, specific protein blood analysis and cancer marker detection on a serum sample.

However, in some cases, the integrity of the serum sample may affect the accuracy of the results of the clinical analyzer. For example, preanalytical variables in the serum sample, such as Hemolysis (ruptured red blood cells), Icteris (excessive Bilirubin) and Lipemia (high, visible lipid content), in excessive amounts, can cause some clinical analyzers to indicate a "problem" with the sample and in some cases provide inaccurate analytical results.

One way to evaluate the integrity of the serum sample is to have a skilled laboratory worker visually inspect the color of the serum sample. A normal serum sample has a light yellow to light amber color. Alternately, a serum sample containing hemoglobin caused by hemolysis is reddish in color; a sample containing excessive bilirubin is yellow to yellow green in color; and, a sample containing lipids is whitish in color. Thus, the degree of red color in a serum sample corresponds to the degree of sample hemolysis; the degree of yellow/yellow green color in a sample corresponds to the amount of bilirubin present in the sample; and, the degree of whitish color in a sample corresponds to the amount of lipids present in the serum sample.

Typically, the laboratory worker will assign an hemolytic index, an icteric index and a lipemic index to the serum sample based upon the color. Based upon the value of the hemolytic index, the icteric index and the lipemic index, the quality of the results from the clinical analyzer can be evaluated. Alternately, if the value of one or more of the hemolytic index, the icteric index and the lipemic index are too high, the serum sample will be discarded without analysis by the clinical analyzer.

However, visual inspection can be labor intensive and costly. Further, the possibility of human error exists with visual inspection, the results of the visual inspection is highly subjective and varies between workers, and one of the variables could mask or hide the other variables. Furthermore, with closed container sampling, bar code labels directly on the container, and automated clinical analyzers, the laboratory worker, in many instances simply does not have an opportunity to visually observe the serum sample.

Thus, it is becoming increasing important to evaluate the integrity of the serum sample without the use of visual inspection by a laboratory worker.

One attempt to solve this problem involves optically viewing the serum sample after the serum sample has been transferred to one of the cuvettes of the clinical analyzer. Measuring the optical characteristics of the sample in the clinical analyzer eliminates the need for visual inspection. However, this test will use machine time of the clinical analyzer and if the integrity of the serum sample is determined to be compromised, machine time and a machine cycle am waited. Further, this procedure can not be used with clinical analyzers which add reagents to the cuvette prior to adding the serum sample.

Another attempt to solve the problem involves separately testing a portion of the serum sample in a separate cuvette of the clinical analyzer, simultaneously with the other tests being performed on the serum sample by the clinical analyzer. However, this requires the use of a portion of the sample and the clinical analyzer. Therefore, this procedure will waste sample and machine time. Further, with this procedure, if the serum sample is determined to be compromised, a number of machine cycle and reagents are wasted.

Additionally, if the integrity of the sample is evaluated in the clinical analyzer, the cuvette must be washed to prevent carry-over between serum samples. This results in an increased amount of waste fluid being used to wash the cuvette. For large scale operations, the increased amount of fluid poses several problems including increased costs, reduced output, and increased environmental concerns.

In light of the above, it is an object of the present invention to provide a method and device which evaluates the integrity of a serum sample, without visual inspection by a laboratory worker. Another object of the present invention is to provide a method and device which quickly and accurately determines the presence of Hemolysis, Icteris and Lipemia in a sample, without consuming any sample and without adversely effecting the integrity of the sample. Yet another object of the present invention is to provide a method and device which establishes a hemolytic index, an icteric index and a lipemic index for the serum sample, without wasting machine time of the clinical analyzer and without interrupting the operation of the clinical analyzer. Still another object of the present invention is to provide a method and device which evaluates the integrity of the sample and transfers the sample to an appropriate location based upon the integrity of the sample.

SUMMARY OF THE INVENTION

The present invention is directed to a method and device for evaluating the integrity of a serum sample in a sample container which satisfies these objectives. The method disclosed herein includes the steps of: (i) positioning a probe inlet of a probe in a sample container; (ii) aspirating at least a portion of the serum sample into a probe lumen of the probe from the sample container; and (iii) monitoring the serum sample in the probe lumen to determine whether at least one of the serum variables is present in the serum sample.

Thus, the serum sample is evaluated in the probe lumen, prior to being transferred to a clinical analyzer. Therefore, machine time of the clinical analyzer is not wasted, the serum sample is not consumed or altered and the serum sample can be transferred to an appropriate location, e.g., the clinical analyzer or a waste receptacle, based upon results of the evaluation.

The following terms used in this application shall have the following meaning:

"Serum Variables" shall mean and include hemolysis, icteris, lipemia and other variables which may affect the accuracy of the results of the clinical analyzer.

"Hemolytic index" shall mean the grade given to a particular sample based upon the estimated content of hemolysis present in the sample. Generally, the grading scale for visual observation ranges from zero through four (0–4). Zero represents substantially no hemolysis while four represents significant hemolysis. Alternately, the scale could be 0–10, 0–20, A–F or some other range.

"Icteric index" shall mean the grade given to a particular sample based upon the estimated content of icteris present in the sample. Generally, the grading scale for visual observation ranges from zero through four (0–4). Similarly, zero represents substantially no icteris, while four represents significant presence of icteris. Alternately, the scale could be 0–10, 0–20, A–F or some other range.

"Lipemic index" shall mean the grade given to a particular sample based upon the estimated content of lipemia present in the sample. Generally, the grading scale for visual observation ranges from zero through four (0–4). Similarly, zero represents substantially no lipemia, while four represents significant presence of lipemia. Alternately, the scale could be 0–10, 0–20, A–F or some other range.

"Serum Indices" shall mean and include the hemolytic index, the icteric index and the lipemic index.

"Predetermined Value" shall mean a value for the hemolytic index, the icteric index or the lipemic index at which the integrity of the sample for testing may be considered to be compromised. The predetermined value varies according to the scale of the serum indices, which of the serum indices is in question and the tests to be performed by the clinical analyzer or other device. For example, if the hemolytic index is rated on a scale of 0–4, a hemolytic index of 3 could be considered to compromise the sample for some tests. Thus, the predetermined value in this example would be 3. Alternately, a reading of 2 on a scale of 0–4 for the icteric index could be unacceptable in some instances. Thus, for this example, the predetermined value is 2.

"Spectrophotometric analysis" shall mean and include measuring optical absorbence, turbidimetric analysis and/or nephelometric analysis. Preferably, the serum sample is monitored to determine whether the serum variables, hemolysis, icteris and lipemia are present in the sample. More preferably, the method includes the step of determining the hemolytic index, the icteric index and the lipemic index of the serum sample. This will allow the laboratory to determine whether the sample is suitable for testing with the clinical analyzer and will allow results from the clinical analyzer to be properly evaluated.

Also, the method can include the step of transferring the sample from the probe lumen to one of two receptacles based upon the results of the spectrophotometer analysis of the sample. For example, the sample can be transferred to a first receptacle, e.g., a waste receptacle, if one of the serum indices is above the predetermined value or the sample is transferred to a second receptacle, e.g., the clinical analyzer or a sample splitter if all of the serum indices are below the predetermined value.

The invention is also a probe which includes a needle, a substantially transparent section, e.g., a flow cell and a detector. The needle has a probe inlet which is disposed within the sample container, a needle lumen for receiving at least a portion of the serum sample from the sample container and a needle output. The flow cell includes a cell lumen which is in fluid communication with the needle output.

The needle lumen and the cell lumen cooperate to define a probe lumen having a substantially constant diameter proximate the substantially transparent section. Stated another way, the needle lumen has an inner diameter which is substantially equal to an inner diameter of the cell lumen. The detector utilizes spectrophotometric analysis of the sample, through the flow cell to determine the presence of the serum variables. As provided herein, the hemolytic index, the icteric index and the lipemic index of the serum sample can be determined, from the results of the spectrophotometric analysis.

It is important to recognize that with the present invention, the integrity of the sample is tested within the probe, without using a laboratory worker. Further, the method and probe quickly and accurately determine the level of the serum indices, without consuming any serum sample and without adversely effecting the integrity of the sample. Furthermore, since the serum indices are determined while the sample is in the probe, before transferring the sample to the clinical analyzer, a machine cycle is not wasted and the operation of the clinical analyzer is not interrupted.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
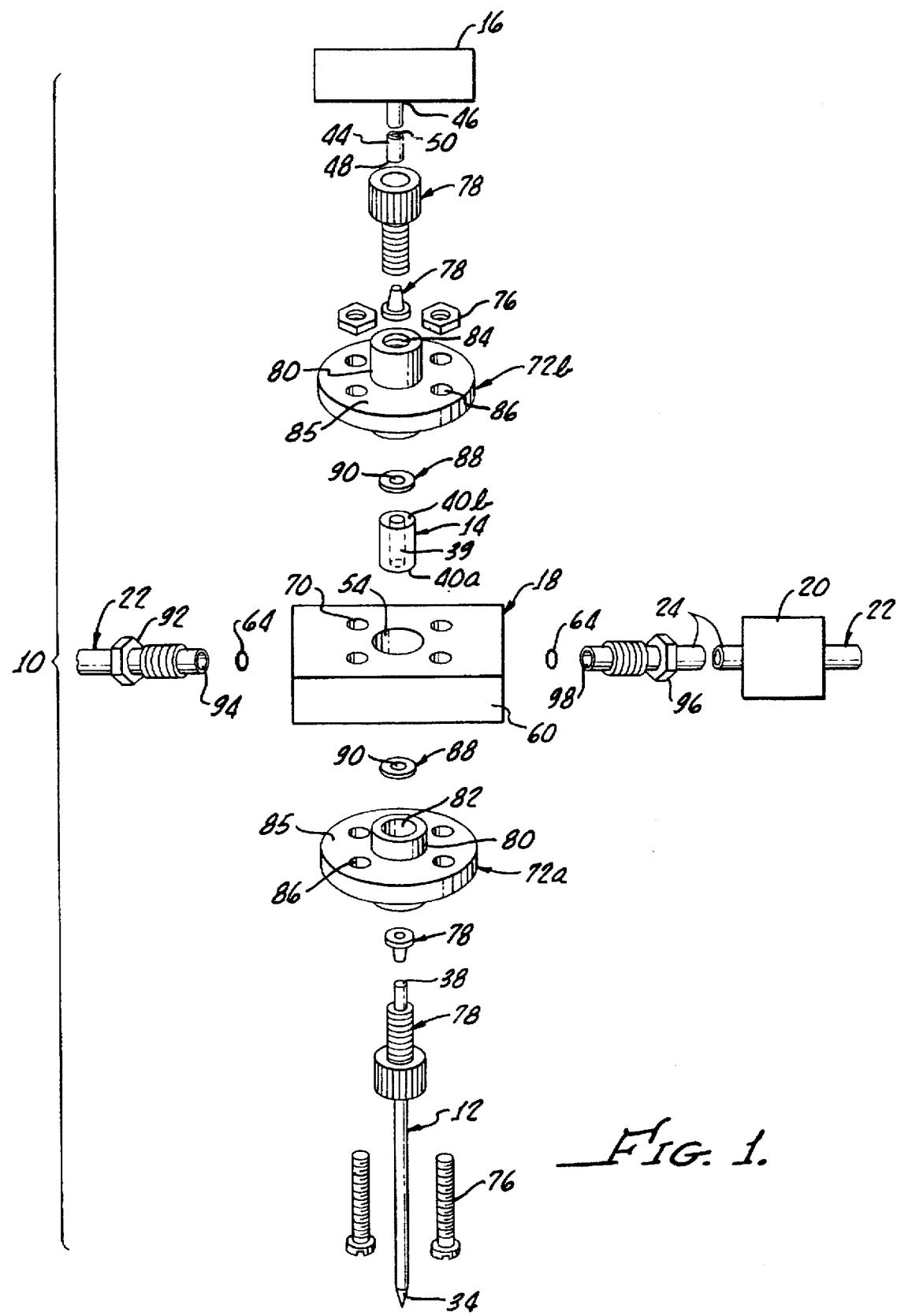
FIG. 1 is an exploded perspective view of a probe having features of the present invention.

Referring initially to FIG. 1, a probe 10 according to the present invention includes: (i) a needle 12; (ii) a substantially transparent section 14; (iii) an aspirator 16; (iv) an optics block 18; and (v) a detector 20 including an optics input 22 and an optics output 24 for monitoring the substantially transparent section 14. As described in detail below, the probe 10 is particularly useful for determining a hemolytic index, an icteric index and a lipemic index for a serum sample 26 (shown in FIG. 4) prior to transferring the serum sample 26 to a clinical analyzer 30 in FIG. 4. However, the probe 10 may be useful for transferring other biological samples such as, urine or cerebral spinal fluid.

Figure 2:
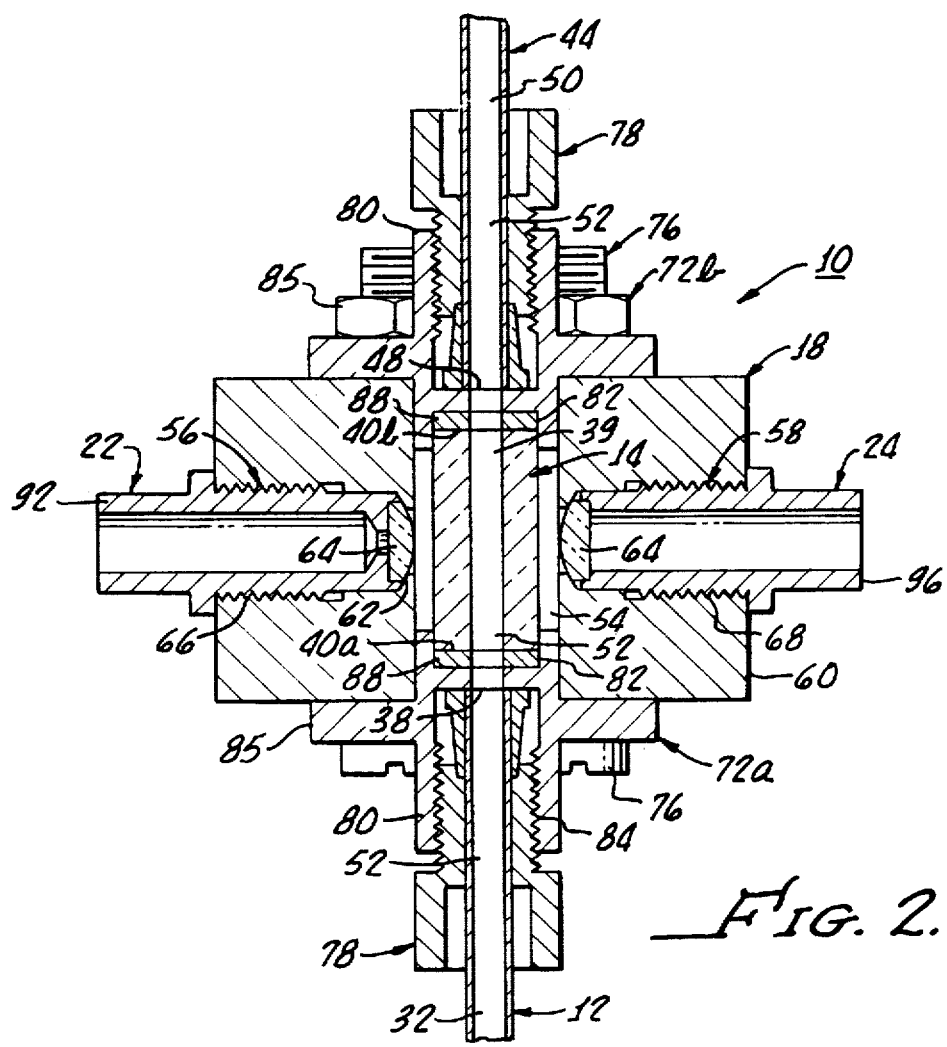
FIG. 2 is a side, assembled, cross-sectional view of a portion of the probe of FIG. 1.

Referring to FIG. 2, the needle 12 is substantially tubular and defines a needle lumen 32. The needle 12 includes a probe inlet 34 (shown in FIG. 1), which is typically conical shaped, for piercing a lid 36 of a sample container 37 (shown in FIG. 4) and an opposed, open, needle output 38. A suitable needle 12 can be made of fourteen gauge stainless steel.

In the embodiment shown in FIGS. 1 and 2, the substantially transparent section 14 is a tubular flow cell that defines a cell lumen 39. The flow cell has opposed first and second ends 40a, 40b which are substantially parallel and finished to facilitate a smooth, fluid tight assembly with the other components of the probe 10. The first end 40a of the flow cell is connected to and is in fluid communication with the needle output 38 while the second end 40b is in fluid communication with the aspirator 16 as described below.

The flow cell is typically made of precision bore, polished, borosilicate glass or some other substantially transparent material. The flow cell shown in the Figures is approximately one half (½") inches long.

Preferably, the needle 12 is as short as possible and the transparent section 14 is placed as close as possible to the probe inlet 34, consistent with the need for the probe inlet 34 to extend to a bottom 42 of the sample container 37. This will reduce the distance in which bubbles, which can distort the results of the detector 20 can form.

Typically, a needle 12 which is between approximately 4 inches long will extend to the bottom 42 of most sample containers 37. Therefore, the transparent section 14 is preferably located between approximately 4–4½ inches from the probe inlet 34.

The aspirator 16 uses suction to draw or aspirate the sample 26 through the needle lumen 32 to the cell lumen 39. The aspirator 16 must draw a sufficiently large amount of sample 26 or a slug of air (not shown) after some sample 26, so that the sample 26 is aspirated to the cell lumen 39 for evaluation. Subsequently, the aspirator 16 uses pressure to expel the sample 26 from the cell lumen 39 and the needle lumen 32. A motorized syringe sold by Hamilton, located in Nevada makes an excellent aspirator 16.

As previously mentioned, the aspirator 16 is in fluid communication with the second end 40b of the transparent section. In the embodiment shown in the Figures, the aspirator 16 is connected to the transparent section 14 with a tubular member 44, e.g., a piece of tubing. The tubular member 44 has an aspirator end 46 which connects to the aspirator 16 and a cell end 48 which connects to the second end 40b of the transparent section. The tubular member 44 also defines a member lumen 50.

FIG. 2 shows the needle 12, the transparent section 14 and the tubular member 44 assembled. The needle lumen 32, the cell lumen 39 and the member lumen 50 combine to form a probe lumen 52. Preferably, the needle lumen 32, the cell lumen 39 and the member lumen 50 proximate the cell end 48, are substantially, axial aligned, are substantially in-line, and have substantially the same cross-sectional shape and size so as to form a smooth bore. In the present invention, the needle lumen 32, the cell lumen 39 and the member lumen 50 each have a circular cross-section with an inner diameter of approximately 0.06 inches.

The smooth bore reduces dead volumes in the probe lumen 52, thereby reducing carry-over between consecutive samples 26 and reducing the amount of fluid required to clean the probe lumen 52. In high volume testing applications, the reduced waste fluid can result in reduced processing costs, as well as increased ability to comply with environmental regulations. Further, the smooth bore also reduces the turbulence of flow of the sample 26 through the probe lumen 52, which reduces the amount of bubbles created in the sample 26. Reducing the bubbles in the sample 26 increases the sensitivity of the probe 10, because bubbles can obscure optical measurements.

As best seen in FIG. 2, the optics block 18 retains the optics input 22 and the optics output 24 proximate the transparent section 14 and in proper alignment with the cell lumen 39. Preferably, the optics block 18 cooperates with the other components of the probe 10 to substantially enclose the transparent section 14 to reduce stray light reaching the transparent section 14 which can affect the readings of the detector 20.

The optics block 18 is formed from a rigid, substantially opaque material, such as black ABS or similar polymer. The optics block 18 shown in the Figures, is rectangular shaped. Alternately, the optics block 18 can be another shape such as a hexagon, an octagon or a triangle. An advantage of providing a hexagonal shaped optics block 18 is the ease of positioning additional inputs and outputs (not shown) at selected angles with respect to each other, while providing a substantially perpendicular path to the cell lumen 39.

Figure 3:
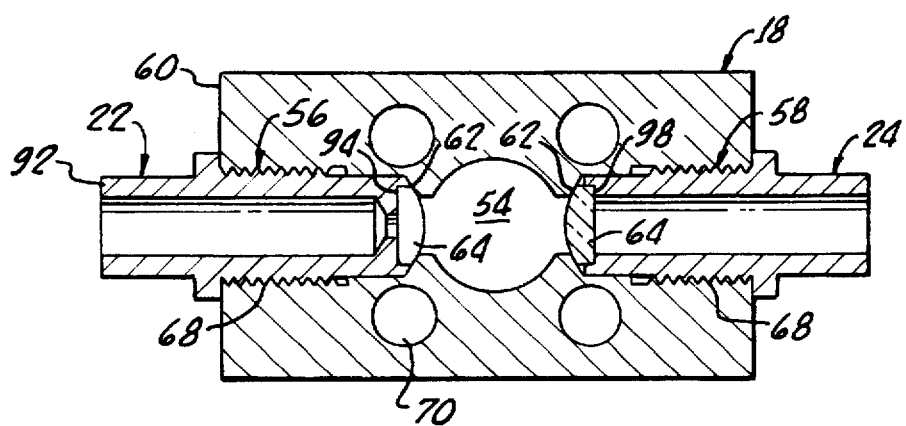
FIG. 3 is a cross-sectional view of an optics block, an optics input and optics output having features of the present invention.

Referring to FIGS. 2 and 3, the optics block 18 includes a central aperture 54 for receiving the transparent section 14, an input opening 56 for receiving the optics input 22 and an output opening 58 receiving for the optics output 24. The input opening 56 and the output opening 58 extend substantially perpendicular to the central aperture 54 and extend from the central aperture 54 of the optics block to an outer perimeter 60 of the optics block. Although, only one input opening 56 and one output opening 58 are shown, dependent upon the application, the optics block 18 can include other openings (not shown) for receiving additional inputs and outputs (not shown).

The input opening 56 and the output opening 58 each include a beveled surface 62 proximate the central aperture 54 which receive a lens 64 for focusing the optics input 22 and optics output 24. In the embodiment shown in the Figures, the input opening 56 also includes an input receiver 66, e.g., an internally threaded surface for attaching the optics input 22 to the optics block 18 and the output opening 58 includes an output receiver 68, e.g., an internally threaded surface, for attaching the optics output 24 to the optics block 18. Those skilled in the art will recognize other ways of attaching the optics input 22 and the optics output 24 to the optics block 18.

Further, in the embodiment shown in the Figures, the optics block 18 includes a plurality of block clearance holes 70 for retaining the optics block 18 to the other components of the probe 10 as provided below.

Referring again to FIGS. 1 and 2, the needle 12, the transparent section 14, the optics block 18 and the tubular member 44 can be secured together with a first end bell 72a, a second end bell 72b, a plurality of bell fasteners 76 and a pair of tube fasteners 78. Alternatively, those skilled in the art will realize other ways to attach these components.

Each end bell 72a, 72b includes a substantially tubular body 80 having a cell opening 82 which is shaped to receive one of the ends 40a, 40b of the flow cell, and an opposed tube fastener receiver 84 for receiving one of the tube fasteners 78. The cell opening 82 and the tube fastener receiver 84 are substantially coaxial to substantially align the needle lumen 32, the cell lumen 39 and the member lumen 50 and provide a smooth flow path. In the embodiment shown in the drawings, each cell opening 82 has a circular cross-section and each tube fastener receiver 84 includes an internally threaded surface.

Each end bell 72a, 72b also includes a disk shaped, bell flange 85 which is attached to and is substantially concentric with the tubular body 80. Each bell flange 85 includes a plurality of flange clearance holes 86 for securing the bell flanges 72a, 72b together. Typically, the end bells 72a, 72b are formed from stainless steel to prevent corrosion.

The end bells 72a, 72b are retained together with the bell fasteners 76. Each bell fastener 76, for example, can be a bolt which passes through one flange clearance hole 86 in the first end bell 72a, one block clearance hole 70 in the optics block, and one flange clearance hole 86 in the second end bell 72b. A nut may be threaded onto the end of the bolt to securely tighten the assembly. Alternately, for example, the flange clearance holes 86 in one or both of the end bells 72a, 72b may be threaded, thereby eliminating the need for a nut.

One of the tube fasteners 78 attaches the needle 12 to the first end bell 72a and the other tube fastener 78 attaches the tubular member 44 to the second end bell 72b. In the embodiment shown in the Figures, each tube fastener 78 is a swage-type compression fittings such as that sold by Upchurch Scientific, located in Washington. Alternately, for example, each tube fastener 78 could be another style of fitting or a weld.

To facilitate a fluid-tight seal between the needle 12, the transparent section 14 and the tubular member 44, a pair of seals 88 are disposed between the flow cell and the cell opening 82 of each end bell 72a, 72b. Typically, each seal 88 is a disk shaped, washer made of a resilient material, such as polyethylene. If the seal 88 is a washer, the washer preferably has a washer aperture 90, having a diameter which is substantially equal to the inner diameter of the cell lumen 39 and which is coaxially aligned therewith to facilitate a relatively smooth probe lumen 52 proximate the cell lumen 39.

The detector 20 is used to determine if any of the serum variables including hemolysis, icteris and lipemia are present in the sample 26. Preferably, the detector 20 also estimates a hemolytic index, an icteric index and an lipemic index for the sample 26. These serum indices allow the laboratory to determine whether the sample 26 is suitable for testing with the clinical analyzer 30 and allow the laboratory to the evaluate the quality of the results from the clinical analyzer 30.

The detector 20 performs a spectrophotometric analysis on the sample 26 in the cell lumen 39 through the transparent section 14. The detector 20 can be implemented in a number of alternate ways. For example, the detector 20 provided herein, measures optical absorbence of the sample 26 in the cell lumen 39. With the absorbence, the detector 20 is able to estimate the serum indices for the sample 26. Alternately, the detector 20 could preform a turbidimetric or nephelometric analysis of the sample 26 while the sample 26 is in the transparent section 14.

The design of a detector 20 which measures optical absorbence can also vary. For example, the detector 20 described in detail herein includes an optics input 22 providing input at five separate wavelengths and a single optics output 24. Alternately, for example, the optics input 22 could provide input at more than or less than five wavelengths and the optics output 24 could include a plurality of filters and receivers.

As provided herein, the optics input 22 includes a bundle of five (5) separate fiber-optics fibers (not shown) which are secured to the optics block 18 with an optics input fitting 92. The optics input fitting 92 includes an externally threaded surface for engaging the input receiver 66 and a protruding lip 94 for retaining one of the lens 64 against the beveled surface 62.

Each of the separate fiber-optics fiber transmits light at a separate wavelength. Each separate wavelength can be provided by a separate light-emitting diode (LED) which is in optical communication with the fiber-optics fibers. Light from each LED can be transferred to the respective fiber-optics fiber in a number of alternate ways. For example, the LED lens can be machined and polished to within a few thousands of an inch of a wire bond (not shown) on the LED. The machined LEDs are then retained in a substantially enclosed remote box (not shown) with an epoxy (not shown) and each fiber-optics fiber is brought into contact with the machined end of its respective LED.

The optics input 22 also includes a LED drive circuit (not shown) which to sequentially activates each of the five LEDs. Each LED is sequentially activated to test the spectral characteristics of the sample at that particular wavelength. The spectral characteristics of the sample could be tested using LEDs emitting any wavelength of light desired, depending upon the application. For example, the five LEDs utilized can be blue, emerald-green, green, yellow, and red. The LED drive circuit can also be housed in the remote box.

The optics output 24 includes a single large diameter fiber-optics fiber (not shown) which is secured to the optics block 18 with an optics output fitting 96 and a silicon photodiode detector (not shown). The optics output fitting 96 includes an externally threaded surface for engaging the output receiver 68 and a forwardly protruding lip 98 for retaining one of the lens 64 against the beveled surface 62.

Light passing through the cell lumen 39 from the optics input 22 is collected by the large fiber-optics fiber of the optics output 24. Light is then transferred through the large diameter fiber-optics fiber to the silicon photodiode detector which measures the amount of light received through the cell lumen 39. A suitable silicon photodiode detector is sold by Burr Brown, located in Arizona.

The detector 20 also includes a logic circuit (not shown) for determining the absorbence at the five wavelengths. From these absorbences, the logic circuit can estimate the serum indices. Once the serum indices are determined, depending on the results, the sample 26 can be transferred to the clinical analyzer for further testing or disposed of in a waste container. Typically, the detector 20 will report to the laboratory computer, print or display the results from the spectrophotometric analysis so that the laboratory can evaluate what to do with the sample 26.

Additionally, light scatter through the sample may be collected and transmitted via another fiber-optic cable output (not shown) to a second detector (not shown) which may be used to perform nephelometric or turbidimetric analysis of the sample 26. As described above, the optics block 18 can be modified to allow collecting light from a plurality of fixed angles, through the cell lumen 39.

Figure 4:
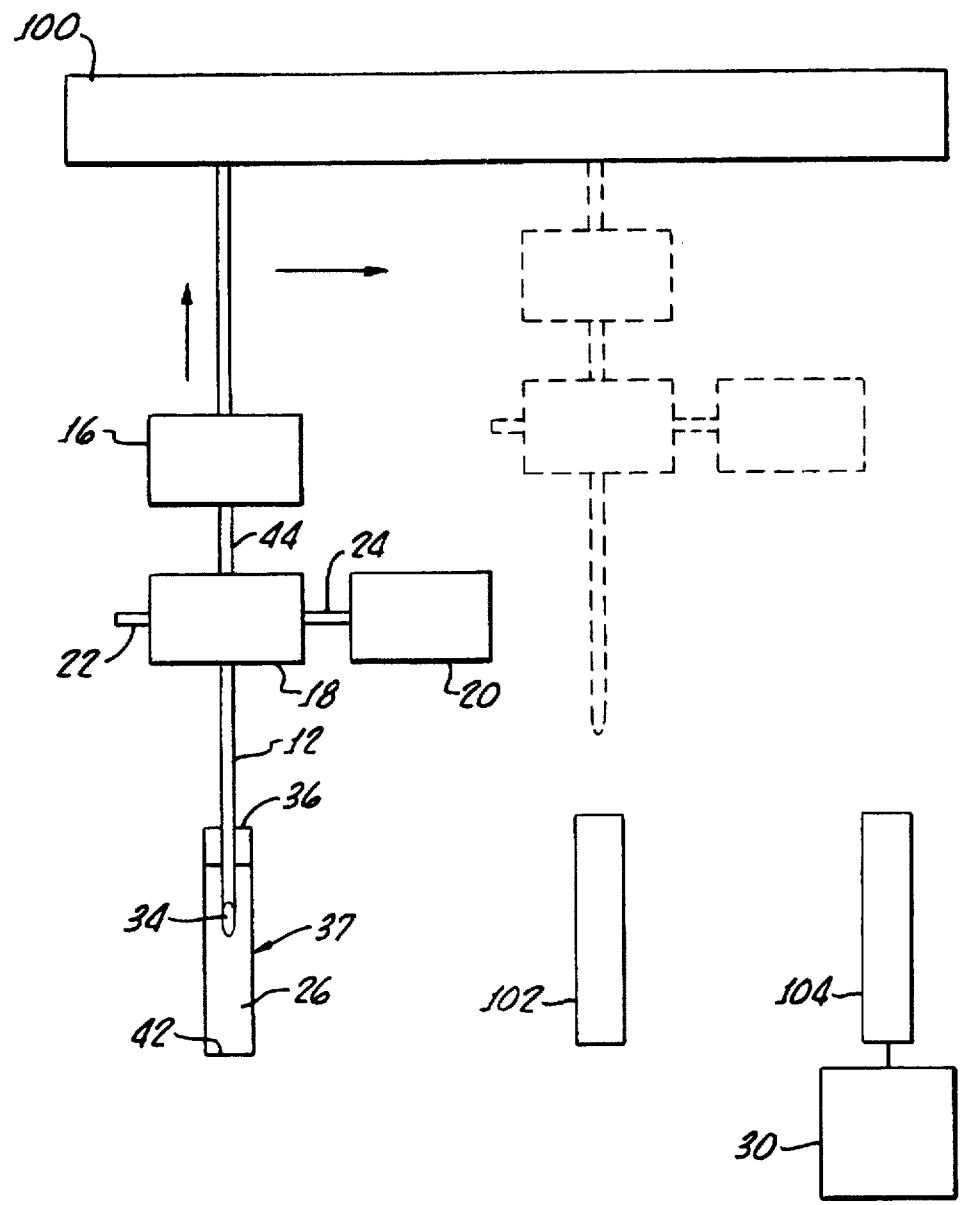
FIG. 4 is a simplified plan view of the probe of FIG. 1 configured for operation in accordance with the present invention.

Preferably, as shown in FIG. 4, the present invention includes a mover 100 which selectively allows the probe 10 to move relative to the sample container 37, a first receptacle 102 and a second receptacle 104. This allows the probe 10 to transfer the sample 26 from the probe lumen 52 to one of the receptacles 102, 104 based upon the results from the detector 20. For example, the mover 100 can be a robotic arm which moves the probe 10 to the proper position in the first receptacle 102 or the second receptacle 104. Alternately, the mover 100 can be a device which moves the sample container 37 and the receptacles 102, 104 relative to the probe 10.

Depending upon the particular embodiment, the first receptacle 102 and second receptacle 104 can, for example be either a cuvette for a sample analyzer 30, a cuvette for a sample splitter, a waste receptacle or the sample container 37. A clinical analyzer 30 sold by the assignee of the present invention, under the trademark Synchron CX®7, can be utilized with the present invention.

The key advantage of this invention is that it increases the throughput of a clinical analyzer by determining if the sample 26 is suitable for testing prior to placing the sample 26 in the clinical analyzer 30.

OPERATION

An example of the operation of a probe 10 having features of the present invention can best be visualized with reference to FIGS. 1 and 4. The operation can begin with the probe lumen 52 being filled with wash solution (not shown) which cleans the probe lumen 52. With the wash solution in the cell lumen 39, the detector 20 takes measurements to establish a zero or a 100% transmission value for the detector 20. This is accomplished by having the LED drive circuit sequentially activate each of the LEDs. Light from the LEDs is transferred to the cell lumen 39 via the five fiber optics fibers. Light from the cell lumen 39 is collected with the large fiber optics fiber and transferred to the silicon photodiode detector of the detector 20. Preferably, each LED is activated at least twenty times and the measurements for each LED are averaged to eliminate electronic noise.

Next, the detector 20 takes measurements, without light input from the LEDs, to establish an offset for the detector, i.e., to compensate for stray light and electronic drifts. Again, twenty measurements are averaged to obtain a single value for the offset for each wavelength.

Subsequently, the mover 100 moves either the probe 10 or the sample container 37 so that the probe inlet 34 pierces the lid 36 of the sample container 37. Next, a portion of the serum sample 26 is aspirated from the probe inlet 34 to the cell lumen 39 with the aspirator 16.

With the serum sample 26 in the cell lumen 39, the detector 20 again causes the LED drive circuit to sequentially activate each of the LEDs. Measurements are collected by the silicon photodiode detector. Again, each LED is preferably activated at least twenty times and the measurements for each LED are averaged to eliminate noise.

From these measurements, the logic circuit of the detector 20 determines whether hemolysis, icteris and lipemia are present in the sample 29. Preferably, from these measurements, the detector 20 estimates the hemolytic index, the icteric index and the lipemic index in the serum sample.

Preferably, the probe 10 also transfers the sample 26 from the probe 10 to either the first or second receptacles 102, 104 based upon the measurements from the detector 20. For example, if one of the serum indices is above a predetermined value, the mover 100 moves the probe 10 or the first receptacle 102 so that the sample 26 is transferred to the first receptacle 102, e.g., a waste reservoir. Alternately, if all the serum indices are below the predetermined value, the mover 100 moves the probe 10 or the second receptacle 104 so that sample 20 is transferred to the second receptacle 102, e.g., the clinical analyzer.

As previously mentioned, the predetermined value varies according to the scale of the serum indices, which of the serum indices is in question, and the tests to performed by the clinical analyzer 30 or other device. For example, if the hemolytic index, the icteric index and the lipemic index are rated on a scale of 0-4, and a value of 3 for the hemolytic index, a value of 2 for the icteric index or a value of 2 for the lipemic index could effect the results from a particular clinical analyzer, the predetermined value of the hemolytic index is 3, the predetermined value for the icteric index is 2 and the predetermined value for the lipemic index is 2.

In this situation, if the detector 20 determines that the hemolytic index is 3 for a particular sample 26, the sample 26 would be transferred from the probe 10 to the first receptacle 102, i.e., a waste reservoir. Alternately, if the hemolytic index is only two (2), the icteric index is one (1) and the lipemic index is (one) (1), the sample 26 would be suitable for testing with the clinical analyzer 30 and the sample 26 would be transferred from the probe to the second receptacle 104.

While the particular probe 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for determining the presence of hemolysis, icterus, or lipemia, in a neat serum sample contained in a sample container, the method comprising the steps of:

positioning a probe inlet of a probe in the sample container;

aspirating at least a portion of the neat serum sample from the sample container, into a probe lumen of the probe; and monitoring the neat serum sample in the probe lumen to determine whether at least one of hemolysis, icterus, and lipemia is present in the neat serum sample.

2. The method of claim 1 wherein the probe includes a substantially transparent section and the monitoring of the neat serum sample occurs; through the substantially transparent section.

3. The method of claim 1 wherein the probe includes a substantially transparent flow cell and the monitoring of the neat serum sample occurs through the flow cell.

4. The method of claim 1 wherein the step of monitoring the neat serum sample includes a spectrophotometric analysis of a portion of the neat serum sample in the probe lumen at at least two alternate wavelengths.

5. The method of claim 1 wherein the step of monitoring the neat serum sample includes monitoring the neat serum sample to determine the presence of hemolysis, icterus and lipemia in the serum sample.

6. The method of claim 1 comprising the step of determining at least one of the serum indices of the neat serum sample in probe lumen.

7. The method of claim 1 comprising the step of determining a hemolytic index, an icteric index and a lipemic index of the neat serum sample in the probe lumen.

8. A method for determining at least one serum index of a neat serum sample retained in a sample container, the method comprising the steps of:

positioning a probe inlet of probe in the sample container;

aspirating at least a portion of the neat serum sample into a probe lumen of the probe;

performing a spectrophotometric analysis of the neat serum sample through a substantially transparent section of the probe; and determining at least one serum index of the neat serum sample based upon the spectrophotometric analysis of the neat serum sample in the probe lumen.

9. The method of claim 8 including the step of determining all of the serum indices of the neat serum sample.

10. The method of claim 9 comprising the step of transferring the neat serum sample from the probe lumen to a first receptacle if one of the serum indices of the neat serum sample in the probe lumen is above a predetermined value.

11. The method of claim 10 comprising the step of transferring the neat serum sample from the probe lumen to a second receptacle if all of the serum indices of the neat serum sample in the probe lumen are below the predetermined value.

12. The method of claim 8 wherein the step of preforming a spectrophotometric analysis includes measuring the optical absorbence of the neat sample at at least three alternate wavelengths.

13. A method for transferring a sample from a sample container to one of two receptacles, the method comprising the steps of:

positioning a probe inlet of probe in the sample container;

aspirating at least a portion of the sample into a probe lumen of the probe;

preforming a spectrophotometric analysis of the sample through a substantially transparent section the probe and;

transferring the sample from the probe lumen to one of the two receptacles based upon the results of the spectrophotometric analysis of the sample in the probe lumen.

14. The method of claim 13 wherein the sample is a neat serum sample and the method comprising the step of determining whether at least one of hemolysis, icterus, and lipemia is present in the neat serum sample from the spectrophotometric analysis.

15. The method of claim 13 wherein the sample is a neat serum sample and the method comprising the step of determining at least one of the serum indices of the neat serum samples from the spectrophotometric analysis.

16. A device for determining the presence of hemolysis, icterus, or lipemia in a neat serum sample, contained in a sample container, the device comprising;

a probe having a probe inlet and a probe lumen, the probe inlet being adapted for being disposed within the sample container; and a detector for monitoring the probe lumen to determine the presence of at least one of hemolysis, icterus, and lipemia in the neat serum sample in the probe lumen.

17. The device of claim 16 wherein the detector determines whether hemolysis, icterus and lipemia are present in the neat serum sample.

18. The device of claim 16 wherein the detector also determines at least one of the serum indices of the neat serum sample.

19. The device of claim 16 wherein the probe lumen includes a needle lumen and a cell lumen and an inner diameter of the needle lumen is substantially equal to an inner diameter of the cell lumen.

20. The device of claim 16 wherein the detector performs a spectrophotometric analysis the neat serum sample in the probe lumen.

21. The device of claim 20 including a mover which enables the probe to transfer the neat serum sample from the probe to one of at least two containers based upon the spectrophotometric analysis of the neat serum sample in the probe lumen.

22. A device which is useful for performing a preliminary screening test on a sample from a sample container and transferring the sample to one of at least two receptacles based upon the results of the preliminary screening test, the device comprising:

a probe having a probe inlet for being disposed within the sample container and a probe lumen for receiving at least a portion of the sample from the sample container;

a detector for performing the preliminary screening test on the sample in the probe lumen; and a mover which enables the probe to transfer the sample from the probe lumen to one of the receptacles based upon the preliminary screening test performed on the sample in the probe lumen.

23. The device of claim 22 wherein the probe lumen includes a needle lumen and a cell lumen and an inner diameter of the needle lumen is substantially equal to an inner diameter of the cell lumen.

24. The device of claim 22 wherein the sample is a neat serum sample and the detector determines serum indices for the neat serum sample based upon spectrophotmetric analysis and the mover enables the device to transfer the neat serum sample from the probe to one of the receptacles if one of the serum indices is above a predetermined value and enables the device to transfer the neat serum sample from the probe to the ether one of the receptacles if all of the serum indices are below the predetermined value.

25. A clinical analyzer including the device of claim 22.

26. A clinical analyzer including the device of claim 16.

27. A device for performing a preliminary screening test to determine the presence of at least one serum variable in a neat serum sample contained in a sample container, the device comprising:

a probe having a probe inlet and a probe lumen, the probe inlet being adapted for being disposed within the sample container; and a detector for performing a preliminary screening test on the neat serum sample in the probe lumen to determine the presence of at least one serum variable.

28. A method for performing preliminary screening test to determine the presence of at least one serum variable in a neat serum sample contained in a sample container, the method comprising the steps of:

positioning a probe inlet of a probe in the sample container containing the neat serum sample;

aspirating at least a portion of the neat serum sample from the sample container into a probe lumen of the probe; and monitoring the neat serum sample in the probe lumen to determine whether at least one of the serum variables is present in the neat serum sample.

* * * * *